United States Patent [19]

Pitchen et al.

[11] Patent Number: 5,780,636
[45] Date of Patent: Jul. 14, 1998

[54] PROCESS FOR THIOPYRANS

[75] Inventors: Philippe Pitchen; David Michael Thompson, both of Dagenham, United Kingdom

[73] Assignee: Rhone-Poulenc Rorer Limited, Eastbourne, England

[21] Appl. No.: 583,363

[22] Filed: Jan. 5, 1996

Related U.S. Application Data

[63] Continuation of PCT/GB94/01472, Jul. 7, 1994.

[30] Foreign Application Priority Data

Jul. 8, 1993 [GB] United Kingdom ............... 9314133

[51] Int. Cl.$^6$ ............... C07D 409/04
[52] U.S. Cl. ............... 546/280.1
[58] Field of Search ............... 546/280.1

[56] References Cited

U.S. PATENT DOCUMENTS 4,568,682  2/1986  Aloup et al. .
5,120,852  6/1992  Aloup et al. .

FOREIGN PATENT DOCUMENTS 0 426 557  5/1991  European Pat. Off. .

OTHER PUBLICATIONS

J. Med. Chem., vol. 35, No. 20, 1992, 3613–3624, Brown wt. al., Synthesis and Biological Activity of trans–(±)–N–Methyl–2–(3–pyridyl)–2–tetrahydrothiopyrancarbothio-amide 1–Oxide (RP 49356) and Analogues: A New Class of Potassium Channel Opener.

*Primary Examiner*—C. Warren Ivy
*Assistant Examiner*—Charanjit S. Aulakh
*Attorney, Agent, or Firm*—Raymond S. Parker, III; Paul R. Darkes; Martin F. Savitzky

[57] ABSTRACT

The invention relates to a process for the preparation of intermediates useful in the preparation of (1R,2R)-2-(3-pyridyl)-N-alkyltetrahydro-2H-thiopyran-2-carbothioamide 1-oxides, which possess useful pharmaceutical properties, for example antihypertensive properties, and to intermediates and pharmaceutical products prepared using said process.

36 Claims, No Drawings

PROCESS FOR THIOPYRANS

This application is a continuation application of International Application No. PCT/GB/01472, designating the United States, filed Jul. 7, 1994, which, in turn, claims priority to British Application No. GB 9314133.1, filed Jul. 8, 1993.

This invention relates to a process for the preparation of intermediates useful in the preparation of (1R,2R)-2-(3-pyridyl)-N-alkyltetrahydro-2H-thiopyran-2-carbothioamide 1-oxides, which possess useful pharmaceutical properties, for example anti-hypertensive properties, and to intermediates and pharmaceutical products prepared using said process.

In the specifications of European Patent No. 0097584 and its equivalent U.S. Pat. No. 4,568,682 there are described compounds of general formula I, hereinafter depicted, wherein R represents a hydrogen atom or an alkyl group containing 1 to 4 carbon atoms, Het represents an aromatic heterocyclic radical and Y represents a bond or a methylene linkage.

The presence of two asymmetric centres leads to 4 diastereoisomers which may be separated into two racemic pairs of enantiomers which can be designated as "form A" (or the more polar product) and "form B" (or the less polar product), the relative polarity being determined by thin layer chromatography. These two forms may each be resolved, into its enantiomers.

Among the compounds of formula I, form A of 2-(3-pyridyl)-N-methyltetrahydro-2H-thiopyran-2-carbothioamide 1-oxide consists of a mixture of trans isomers which may be represented by formulae II and III, hereinafter depicted.

Studies carried out on isomers II and III have shown that the more active form is isomer III, whose absolute configuration is 1R,2R.

In the specifications of European Patent Application No. 0426557 and is equivalent U.S. Pat. No. 5,120,852 there is described a process for the preparation of compounds of general formula IV, hereinafter depicted, wherein $R^1$ represents a straight- or branched-chain alkyl group containing 1 to 4 carbon atoms by the action of an alkyl isothiocyanate of the general formula:

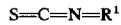

$$S=C=N=R^1 \qquad V$$

wherein $R^1$ is as hereinbefore defined, on the anion derived from a sulphoxide of formula VI or VII, hereinafter depicted, or on the anions derived from mixtures thereof.

According to the specifications of the aforementioned European Patent Application No. 0426557 and U.S. Pat. No. 5,120,852, the compounds of formulae VI and VII may be prepared by the selective oxidation, by chemical or biochemical means, of the compounds of formula VIII, hereinafter depicted, which generally occur in the racemic form.

According to the present invention, (1R,2R)-2-(3-pyridyl) tetrahydro-2H-thiopyran 1-oxide of formula VI or (1R,2S)-2-(3-pyridyl)-tetrahydro-2H-thiopyran 1-oxide of formula VII, or mixtures thereof, are prepared by the reduction of (R)-6-(3-pyridyl)-3,4-dihydro-2H-thiopyran 1-oxide of formula IX, hereinafter depicted, which, according to a further feature of the invention, is prepared by the stereoselective oxidation of 6-(3-pyridyl)-3,4-dihydro-2H-thiopyran of formula X, hereinafter depicted.

The preparation of (1R,2R)-2-(3-pyridyl)-tetrahydro-2H-thiopyran 1-oxide of formula VI or (1R,2S)-2-(3-pyridyl) tetrahydro-2H-thiopyran 1-oxide of formula VII, or mixtures thereof, by the reduction of (R)-6-(3-pyridyl)-3,4-dihydro-2H-thiopyran 1-oxide of formula IX is carried out by the application or adaptation of known stereoselective reducing systems, for example by means of a metal borohydride, for example sodium borohydride, preferably in a convenient solvent, such as a lower alcohol, e.g. ethanol.

The enantiomeric purity, i.e. the enantiomeric excess, of the (1R,2R)-2-(3-pyridyl)tetrahydro-2H-thiopyran 1-oxide of formula VI can be enhanced to values approaching 100% by recrystallisation from suitable solvent systems, for example ethyl acetate, toluene, methyl ethyl ketone, mixtures of methyl ethyl ketone with tert-butyl methyl ether, and mixtures of methyl ethyl ketone with acetone.

(R)-6-(3-Pyridyl)-3,4-dihydro-2H-thiopyran 1-oxide of formula IX is a new compound and is a feature of the present invention.

The preparation of (R)-6-(3-pyridyl)-3,4-dihydro-2H-thiopyran 1-oxide of formula IX by the stereoselective oxidation of 6-(3-pyridyl)-3,4-dihydro-2H-thiopyran of formula X is preferably carried out by the application or adaptation of known stereoselective oxidising systems, for example a mixture of a dialkyl L-tartrate, e.g. diisopropyl L-tartrate or, preferably, diethyl L-tartrate with titanium isopropoxide and an organic hydroperoxide, e.g. tert-butyl hydroperoxide or, preferably, alpha,alpha-dimethylbenzyl hydroperoxide, preferably in a suitable solvent such as dichloromethane, and preferably under an inert atmosphere.

Preferably, for each equivalent of 6-(3-pyridyl)-3,4-dihydro-2H-thiopyran of formula X, there is employed at least 0.1, preferably 0.5 to 1.0, equivalents of titanium isopropoxide, and for each equivalent of titanium isopropoxide, there is employed at least 2, preferably 2 to 4, equivalents of the dialkyl L-tartrate.

As will be appreciated by those skilled in the art, (S)-6-(3-pyridyl)-3,4-dihydro-2H-thiopyran 1-oxide can be prepared in a similar manner but using a dialkyl D-tartrate instead of the dialkyl L-tartrate.

6-(3-Pyridyl)-3,4-dihydro-2H-thiopyran of formula X is also a new compound and is a further feature of the present invention. It is prepared, according to another feature of the invention, by the reaction of a compound of the general formula XI, hereinafter depicted, wherein $R^2$ represents a lower alkyl, preferably methyl, group, or a salt thereof, for example an arylsulphonate or an alkylsulphonate, e.g. the methanesulphonate, with an acid, such as sulphuric or hydrochloric acid, optionally preceded by reaction with a base, e.g. sodium methoxide.

6-(3-Pyridyl)-3,4-dihydro-2H-thiopyran is preferably used soon after preparation or, alternatively, it can be stored in the presence of a base, such as potassium carbonate, preferably in solution in a solvent such as dichloromethane, preferably under an inert atmosphere.

Compounds of formula XI and their salts are also new compounds, and constitute a further feature of the present invention. They are prepared, according to another feature of the invention, from 4-hydroxybutyl 3-pyridyl ketone, by reaction with thioacetic acid, diethyl azodicarboxylate and triphenyl phosphine or, preferably, by reaction with an arylsulphonyl halide or an alkylsulphonyl halide, e.g. toluene-p-sulphonyl chloride or methanesulphonyl chloride, in the presence of a tertiary base such as triethylamine, N,N-diisopropylethylamine or 1,8-diazabicyclo[5.4.0]-undec-7-ene, followed by reaction with thioacetic acid or an alkali metal salt thereof, e.g. potassium thioacetate, followed, if necessary, by formation of the desired salt by known methods, e.g. by reaction with the appropriate acid, e.g. an arylsulphonic or alkylsulphonic acid, e.g. methanesulphonic acid.

4-Hydroxybutyl 3-pyridyl ketone can be prepared by the reaction of an alkyl nicotinate of the general formula XII, hereinafter depicted, wherein $R^3$ represents a lower alkyl, e.g. methyl or ethyl, group, or a 3-pyridyl halide, e.g. 3-pyridyl bromide, with delta-valerolactone in the presence of a base, such as an alkali metal alkoxide, e.g. potassium tert-butoxide, or butyllithium, preferably in an ethereal solvent, such as diethyl ether, tert-butyl methyl ether or tetrahydrofuran.

The following Examples illustrate the invention.

Nuclear magnetic resonance (NMR) spectra are recorded at 200 MHz or 400 MHz. Chemical shifts are expressed in ppm relative to tetramethylsilane. Abbreviations have the usual significances, e.g.: s=singlet, d=doublet, t=triplet, m=multiplet, dd=doublet of doublets, dt=triplet of doublets.

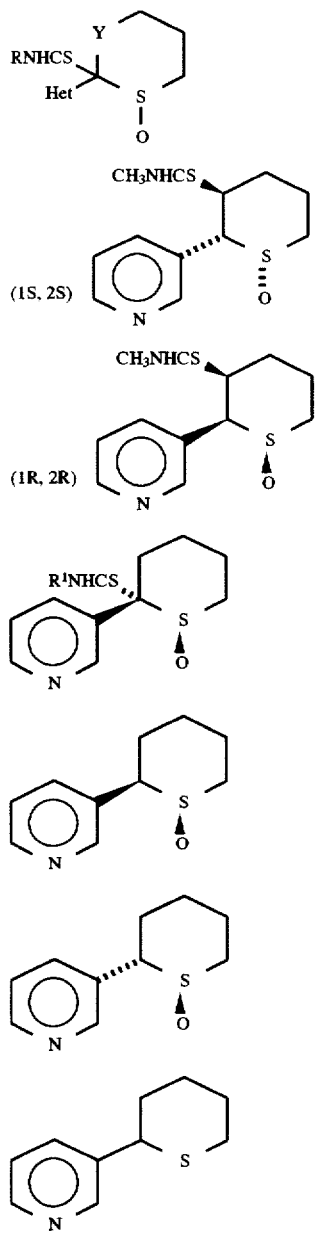

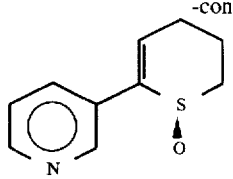

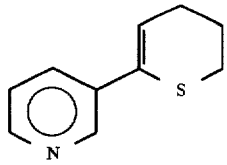

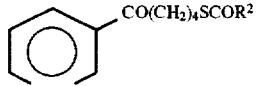

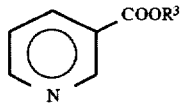

EXAMPLE 1

A stirred solution of potassium tert-butoxide (83.55 g) in tetrahydrofuran (500 ml) under nitrogen at room temperature is treated with a solution of methyl nicotinate (68.5 g) and delta-valerolactone (75.0 g) in tetrahydrofuran (125 ml), continuously during 1 hour, maintaining the temperature between 22° C. and 32° C. The mixture is stirred for 2 hours and is then treated with water (750ml). The resulting mixture is washed with xylene (125 ml) and the aqueous layer is then treated with concentrated hydrochloric acid (400 ml) during a period of 15 minutes, maintaining the temperature between 23° C. and 44° C. The solution is stirred for 90 minutes and then the solution is washed with dichloromethane (250 ml). The aqueous layer is basified to pH8-pH9 by treatment with aqueous sodium hydroxide solution (specific gravity 1.3;480 ml) and then it is washed with xylene* (125 ml) and extracted with dichloromethane (3×250 ml). The combined dichloromethane extracts are dried over magnesium sulphate and the solvent is removed by evaporation under reduced pressure, to give 4-hydroxybutyl 3-pyridyl ketone (49.1 g), in the form of a yellow oil which crystallises to form a pale brown solid, m.p. 36°–38° C. [NMR (CDCl$_3$): 1.7(m,2H), 1.9(m,2H), 3.1(t,2H),3.7(t,2H),7.4(m,1H),8.2 (dt,1H),8.8(m,1H), 9.2(m,1H)].

*This xylene solution is extracted with water (3×100 ml). The aqueous extracts are combined, saturated with sodium chloride and extracted with dichloromethane (3×50 ml). The combined dichloro-methane layers are dried over magnesium sulphate and the solvent is removed by evaporation under reduced pressure, to give a further quantity of the same product (14.0 g).

EXAMPLE 2

A solution of 4-hydroxybutyl 3-pyridyl ketone (66.4 g) in tetrahydrofuran (664 ml) under nitrogen at room temperature is treated with methanesulphonyl chloride (31.6 ml). The mixture is then cooled to 0° C. and treated with N,N-diisopropylethylamine (155 ml), continuously, during 30 minutes, maintaining the temperature below 5° C., and it is stirred for a further period of 10 minutes. The mixture is warmed to 20° C. and is then treated with thioacetic acid during 10 minutes, maintaining the temperature at below 25°

C. The mixture is stirred for 2 hours at 35° C. and is then cooled to 20° C. and treated with water (660 ml). The mixture is extracted twice with t-butyl methyl ether (660 ml and 300 ml). The combined extracts are washed with water (2×1300 ml), dried over magnesium sulphate, then treated with decolourising charcoal (8.7 g) and the mixture is stirred for 10 minutes. After filtration, the solvent is removed by evaporation under reduced pressure, to give S-(4-nicotinoylbutyl) thioacetate (80.7 g) in the form of an oil. This oil is dissolved in t-butyl methyl ether (1200 ml) and the solution is treated with methanesulphonic acid (22.1 ml), dropwise, with stirring, then it is stirred for 1 hour and then cooled to 0° C. for 1 hour. The mixture is filtered and the resulting yellow solid is dried with suction at room temperature, to give 3-(5-acetylmercaptopentanoyl) pyridinium methanesulphonate (91.4 g). m.p. 103°–105° C. |NMR (DMSO-$d_6$):- 1.6(m,2H),1.7(m,2H),2.3(s,3H), 2.4(s, 3H),2.9(t,2H),3.2(t,2H), 7.9(dd,1H),8.7(dt,1H), 9.0(dd,1H), 9.3(d,1H)|.

EXAMPLE 3

A stirred suspension of 3-(5-acetylmercaptopentanoyl) pyridinium methanesulphonate (13.57 g) in methanol (115 ml) at room temperature is treated with a solution of sodium methoxide in methanol (11.75 ml; 30% w/w), during 2 minutes and the resulting solution is stirred for 5 minutes. It is then treated, dropwise, with concentrated sulphuric acid (6.6 ml), during 5 minutes, and the resulting cloudy mixture is heated at reflux for 30 minutes. The mixture is cooled to room temperature, and its pH is then adjusted to 11 by portionwise treatment with aqueous sodium hydroxide solution (82 ml;2M). It is then treated with water (100 ml) and extracted twice with dichloromethane (100 ml and 50 ml). The combined extracts are washed with water (2×115 ml) and dried over magnesium sulphate.

The resulting solution, containing crude 6-(3-pyridyl)-3, 4-dihydro-2H-thiopyran, is used immediately in Example 4. In calculating the amounts of reactants in Example 4 it is assumed that Example 3 has proceeded in 100% yield (7.21 g).

Alternatively, the solution may be stabilised by treatment with anhydrous potassium carbonate (0.4 g) if it is not to be used immediately. If so, the potassium carbonate is filtered off before the solution is used.

EXAMPLE 4

A stirred solution of diethyl L-tartrate (16.80 g) and titanium isopropoxide (11.56 g) in dichloromethane (150 ml) at room temperature is treated with a solution of 6-(3-pyridyl)-3,4-dihydro-2H-thiopyran in dichloromethane |prepared from 13.57 g 3-(5-acetyl-mercaptopentanoyl) pyridinium methanesulphonate as described in Example 3| under nitrogen. The solution is cooled to –20° C. and then treated with alpha,alpha-dimethylbenzyl hydroperoxide (9.1 ml), and the mixture is stirred at –20° C. for 16 hours. The mixture is treated with water (13 ml), and allowed to warm to room temperature, whilst stirring. It is treated with diatomaceous earth (6 g) then filtered through a 1 cm-thick pad of diatomaceous earth. The diatomaceous earth is then washed thoroughly with dichloromethane (3×200 ml). The combined filtrates are washed with aqueous sodium hydroxide solution (300 ml;2M) and then with water (300 ml), dried over magnesium sulphate, and then the solvent is removed by evaporation under reduced pressure to give an oil (15 g). This oil is then subjected to flash chromatography (on 210 g silica gel), eluting with a mixture of ethyl acetate and methanol (80:20 v/v), to give (R)-6-(3-pyridyl)-3,4-dihydro-2H-thiopyran 1-oxide (5.0 g,90.3%ee), in the form of an oil. |NMR (CDCl$_3$):- 2.0(m,1H),2.4(m,2H),2.6(m,1H), 2.8(m,1H), 3.3(m,1H),6.6(dd,1H),7.3(m,1H),7.9(dt,1H),8.6 (dd, 1H), 8.7(m,1H)|.

The percentage enantiomeric excess ("% ee") is determined by chiral HPLC, using the following conditions:- Diacel Chiralcel OD 4.6×250 mm column; mobile phase of heptane/methanol/isopropanol (930:50:20 v/v); flow rate 1.5 ml/min; UV detection at 265 nm; 20 microlitre loop; sample concentration of 0.05% w/v in methanol/isopropanol (1:1 v/v).

EXAMPLE 5

A stirred solution of (R)-6-(3-pyridyl)-3,4-dihydro-2H-thiopyran 1-oxide (22.43 g;88.2%ee) in ethanol (227 ml) is treated, portionwise, with sodium borohydride powder (3.52 g) under nitrogen at room temperature, and the mixture is stirred for 2.5 hours. It is then treated with a further quantity of sodium borohydride (0.43 g), and the mixture is stirred for a further period of 15 minutes. The mixture is treated with water (454 ml) and extracted with dichloromethane (2×340 ml). The combined extracts are washed with water 340 ml), dried over magnesium sulphate and the solvent is removed by evaporation under reduced pressure, to give an oily paste (18.1 g). This paste is treated with ethyl acetate (72 ml) and the mixture is heated at reflux, with stirring. The solution is allowed to cool to room temperature, and stirred for 3 hours. The resulting suspension is cooled to 0° C. for 1 hour, and then filtered. The pale yellow solid is washed with a little cold ethyl acetate and sucked dry using vacuum filtration, to give (1R,2R)-2-(3-pyridyl)tetrahydro-2H-thiopyran 1-oxide (8.03 g;99.7%ee), m.p. 124.5°–126.50° C. |Elemental analysis:- C,61.2;H.6.67; N,7.1 ;S,16.7%. Calculated:- C.61.51 ;H.6.71 ;N,7.17; S,16.42%. NMR (CDCl$_3$):- 1.6(m,1H), 8(m,2H),2.0(m,1H),2.4(m,1H),2.7(m, 2H),3.2(m,1H), 3.5(dd,1H),7.3(m,1H),7.7(dt,1H),8.6(m, 2H)|.

The %ee is determined by chiral HPLC, using the following conditions:- Diacel Chiralcel OD 4.6×250 mm column; mobile phase of heptane/methanol/isopropanol (500:30:5 v/v); flow rate 1.5 ml/min; UV detection at 265 nm; 20 microlitre loop; sample concentration of 0.05% w/v in methanol/isopropanol (1:1 v/v).

EXAMPLE 6

A stirred orange mixture of liquid ammonia (3–5 ml) and ferric nitrate (0.018 g) is treated with sodium (0.177 g), portionwise, under nitrogen. The blue solution formed initially is stirred for 20 minutes, and turns to dark grey. It is then treated with a solution of (1R,2R)-2-(3-pyridyl) tetrahydro-2H-thiopyran 1-oxide (0.75 g) in tetrahydrofuran (9 ml), dropwise, during 2 minutes at –35° C., and the mixture is stirred for 2 minutes. It is then treated with a solution of methyl isothiocyanate (0.41 g) in tetrahydrofuran (1.5 ml) and stirred for 5 minutes at –35° C., then it is treated with ammonium chloride (0.46 g) and is allowed to warm to room temperature. It is then treated with methanol (0.6 ml), and evaporated under reduced pressure, to give a brown paste. This paste is treated with brine (10 ml) and extracted with dichloromethane (3×45 ml). The combined extracts are dried over magnesium sulphate and the solvent is removed by evaporation under reduced pressure, to give a solid (1.18 g). This solid is treated with ethyl acetate (90 ml) and the resulting suspension is stirred and heated at reflux, to give a clear solution. This is cooled to room temperature and stirred for 3 hours. The light brown suspension is filtered with suction and washed with cold ethyl acetate, to give (1R,2R)-2-(3-pyridyl)-N-methyltetrahydro-2H-thiopyran-2-carbothioamide 1-oxide (0.56 g;100%ee), m.p. 215°–216° C. [NMR (CDCl$_3$):- 1.6(m,1H),1.7(m,2H),2.2(m,1H), 2.3 (m,1H),2.9(m,1H),3.0(m,1H),3.1 (d,3H),3.7(m,1H), 7.3(m, 1H),8.1 (m,1H),8.3(m,1H),8.5(m,1H),8.7(m,1H)]; specific rotations (sodium D line) –205° (c=1, 28° C., CHCl$_3$); –281° (c=1, 31° C., EtOH).

The %ee was determined by chiral HPLC using the following conditions:- Diacel Chiralcel OD 4.6×250 mm column; mobile phase of heptane/methanol/isopropanol (880:80:40 v/v); flow rate 1.5 ml/min; UV detection at 265 nm; 20 microlitre loop; sample concentration of 0.05% w/v in methanol/isopropanol (1:1 v/v).

EXAMPLE 7

A solution of potassium tert-butoxide (83.55 g) in tetrahydrofuran (500 ml) at 22° C. is treated, dropwise, with a solution of methyl nicotinate (68.5 g) and delta-valerolactone (75.0 g) in tetrahydrofuran (125 ml) during a period of 1 hour. The solution is then stirred at 23° C. for 2 hours. The reaction mixture is diluted with water and washed with toluene (125 ml). The organic phase is discarded and the aqueous phase is treated dropwise with concentrated hydrochloric acid (400 ml;37% w/v). The solution Is stirred for a further 2 hours. The solution is then washed with dichloromethane (250 ml). The organic phase is discarded and the aqueous phase is treated with aqueous sodium hydroxide solution to bring it to between pH8 and pH9. The aqueous phase is then washed with toluene (125 ml) and the organic phase is back washed with water (3×100 ml). The two aqueous phases are combined and extracted with dichloromethane. The dichloromethane extract is dried over magnesium sulphate, and evaporated to dryness, to give 4-hydroxybutyl 3-pyridyl ketone (61.1 g) in the form of an oil which crystallises to form a pale brown solid, m.p. 36°–38° C. [NMR (CDCl$_3$):- 1.7(m,2H),1.9(m,2H),3.1(t, 2H),3.7(t,2H),7.4(m,1H), 8.2(dt,1H),8.8(m,1H),9.2(m,1H)].

EXAMPLE 8

A solution of 4-hydroxybutyl 3-pyridyl ketone (89.6 g) in tetrahydrofuran (750 ml) under nitrogen at room temperature is treated with N,N-diisopropyl-ethylamine (155.1 g). The mixture is then cooled to 0° C. and treated with methanesulphonyl chloride (63.0 g) continually during 10 minutes, maintaining the temperature at between 5° C. and 10° C., and then the mixture is stirred for 10 minutes. It is then treated with thioacetic acid (45.7 g) during 10 minutes and allowed to warm to 35° C. It is stirred for 1 hour at 35° C. and then cooled to 20° C. It is then treated with water (750 ml) during 5 minutes and the mixture is extracted twice with toluene (750 ml and 350 ml). The combined extracts are washed with water and evaporated, to give S-(4-nicotinoylbutyl) thio-acetate (113.4 g), in the form of an oil.

This oil is treated with tert-butyl methyl ether, followed by decolourising charcoal and, after filtration, treated with methanesulphonic acid (48.1 g), dropwise. The mixture is cooled to 0° C. and filtered and the resulting solid is dried with suction at room temperature, to give 3-(5-acetylmercaptopentanoyl)pyridinium methanesulphonate (139.4 g) in the form of a yellow/orange solid, m.p. 103°–105° C. [NMR (DMSO-d$_6$):- 1.6(m,2H), 1.7(m,2H), 2.3(s,3H),2.4(s,3H), 2.9(t,2H),3.2(t,2H),7.9(dd,1H),8.7(dt, 1H),9.0(dd,1H), 9.3(d,1H)].

EXAMPLE 9

3-(5-Acetylmercaptopentanoyl)pyridinium methanesulphonate (200 g) is treated with hydrochloric acid (780ml; 1N) and the mixture is heated at 65°–70° C. for 5 hours. The contents are cooled to room temperature and then treated with dichloromethane (390 ml). The mixture is treated portionwise with aqueous sodium hydroxide solution to bring it to between pH11 and pH13, and the dichloromethane layer is separated. The aqueous layer is extracted with further dichloromethane (390 ml) and then the combined organic phases are washed twice with brine (3% w/v). The solution, containing 6-(3-pyridyl)-3,4-dihydro-2H-thiopyran, is dried over magnesium sulfate and then treated with potassium carbonate (6 g) and the mixture is stored under nitrogen at 4° C.

EXAMPLE 10

A stirred solution of diethyl L-tartrate (206.2 g) in dichloromethane (760 ml) is treated with a solution (700 ml; prepared as described in Example 9 but filtered just before use) of 6-(3-pyridyl)-3,4-dihydro-2H-thiopyran (88.5 g) in dichloromethane under nitrogen and stirred at room temperature. It is then treated with titanium isopropoxide (71.1 g) and cooled to between –19° C. and –21° C., and treated with a solution of alpha,alpha-dimethylbenzyl hydroperoxide (111 ml) in dichloromethane (110 ml) during 20 minutes and stirred at between –19° C. and –21° C. for 7 hours. The mixture is then treated with hydrochloric acid (2500 ml;1N) and warmed to room temperature, whilst stirring. The aqueous layer is washed with dichloromethane, treated with aqueous sodium hydroxide solution to bring it to between pH11 and pH13, and extracted with dichloromethane (5×800 ml). The combined extracts are washed with an aqueous sodium disulphite solution (5% w/v) which is saturated with sodium chloride (800 ml), dried over magnesium sulphate and evaporated, to give crude (R)-6-(3-pyridyl)-3,4-dihydro-2H-thiopyran 1-oxide in the form of an oil (79.9 g). This oil is then used unpurified in Example 11.

EXAMPLE 11

A stirred suspension of sodium borohydride (11.44 g) in ethanol (935 ml) is treated with a solution of crude (R)-6-(3-pyridyl)-3,4-dihydro-2H-thiopyran 1-oxide (116.9 g; prepared as described in Example 10) in ethanol (117 ml) at room temperature under nitrogen. The mixture is stirred for 3 hours and is then treated with water (935 ml) and acetone (93 ml), with cooling. The solution is extracted with dichloromethane (3×800 ml), the combined extracts are washed with aqueous sodium chloride solution (2×800 ml;25% w/v), dried over magnesium sulphate, and evaporated under reduced pressure to give a paste (96.2 g). This paste is recrystallised from a mixture of tert-butyl methyl ether and methyl ethyl ketone, to give (1R,2R)-2-(3-pyridyl) tetrahydro-2H-thiopyran 1 -oxide (36.16 g), in the form of a pale yellow powder, m.p. 121°–126° C., enantiomeric excess 99.6%. [NMR (CDCl$_3$):- 1.6(m, 1H), 1.8(m,2H),2.0 (m,1H),2.4(m,1H),2.7(m,2H), 3.2(m,1H),3.5(dd,1H),7.3(m, 1H),7.7(dt, 1H), 8.6(m,2H)].

EXAMPLE 12

A stirred suspension of (1R,2R)-2-(3-pyridyl)tetrahydro-2H-thiopyran 1-oxide (50.0 g) in dry tetrahydrofuran (500 ml) is treated with a solution of lithium bis(trimethylsilyl)amide in tetrahydrofuran (281 ml;1M) at between –5° C. and +5° C. The resulting suspension is stirred for 15 minutes at between –5° C. and +50C. and then it is treated with a solution of methyl isothiocyanate (20.26 g) in dry tetrahydrofuran (63 ml) at between –5° C. and +50C. The mixture is stirred at between –5° C. and +5° C. for 30 minutes and then it is treated with water (500 ml). The aqueous phase is then washed with dichloromethane (2×150 ml). The aqueous solution is then treated with charcoal, filtered, neutralised by treatment with dilute hydrochloric acid (2N) and filtered, to give (1R,2R)-2-(3-pyridyl)-N-methyltetrahydro-2H-thiopyran-2-carbothioamide 1-oxide (50.64 g), in the form of a white powder, m.p. 215°–216° C., enantiomeric excess greater than 99.6%. [NMR (CDCl$_3$):- 1.6(m,1H), 1.7(m,2H), 2.2(m,1H),2.3(m, 1H),2.9(m,1H), 3.0(m,1H),3.1 (d,3H),3.7 (m,1H),7.3(m,1H), 8.1 (m,1H),8.3(m,1H),8.5(m,1H),8.7(m, 1H)]; specific rotations (sodium D line) –205° (c=1, 28° C., CHCl$_3$); –281° (c=1, 31° C., EtOH).

EXAMPLE 13

A solution of potassium tert-butoxide (82.14 g) and methyl nicotinate (68.5 g) in tetrahydrofuran (500 ml) is stirred under an atmosphere of nitrogen at 45° C. to 50° C. It is then treated with a solution of delta-valerolactone (75.0 g) in tetrahydrofuran (125 ml) during 2 hours, forming a suspension, which is stirred for 2 hours at 45°–50° C. It is then treated with water (400 ml), followed by concentrated hydrochloric acid (177.0 g) during 15 minutes. The reaction mixture is stirred for 75 minutes at 45°–50° C., then cooled to 20° C. and washed with toluene (2×250 ml). The aqueous layer is basified to pH7.5 by treatment with aqueous sodium hydroxide solution, and is then left standing overnight at ambient temperature, after which the mixture is extracted with toluene (250 ml). Sodium chloride (120 g) is dissolved in the aqueous layer which is then extracted with dichloromethane (4×250 ml). The combined dichloromethane extracts are dried over magnesium sulphate and filtered. This dichloromethane solution is stirred under nitrogen and treated with N,N-diisopropyl-ethylamine (105 ml). The stirred solution is cooled to 0° C. and then treated with methanesulphonyl chloride (42.6 ml), dropwise, keeping the temperature below 10° C. The mixture is washed with water (50 ml), dried over magnesium sulphate and filtered. The filtrate is stirred and cooled in an ice-bath. It is then treated with methanesulphonic acid (32.5 ml) during 5 minutes, the mixture is stirred for 10 minutes, then treated with tert-butyl methyl ether (150 ml), dropwise during 20 minutes. The resulting suspension is stirred, with cooling in an ice-bath, until crystallisation is complete, to give 3-(5-methanesulphonyl-pentanoyl)pyridinium methanesulphonate (112.1 g), in the form of a white powder, m.p. 74° C.

EXAMPLE 14

A solution of 3-(5-methanesulphonyl-pentanoyl) pyridinium methanesulphonate (35.3 g) in tetrahydrofuran (200 ml) is treated with N,N-diisopropylethylamine (39 ml) and the resulting solution is stirred for 10 minutes. It is then treated with thioacetic acid (8.25 ml), dropwise, and the mixture is stirred at ambient temperature for 17 hours. It is then treated with water (200 ml), the mixture is stirred for 5 minutes, and the product is then extracted into toluene (150 ml;75 ml). The combined organic solution is washed with aqueous sodium chloride solution (250 ml), dried over magnesium sulphate and filtered. The filtrate is extracted with hydrochloric acid (1N;2×125 ml). The acid solution is then stirred at reflux for 2 hours, cooled to room temperature and washed with toluene (50 ml). The aqueous layer is stirred with charcoal (0.5 g) and filtered. This filtrate is stirred with dichloromethane (75 ml) and it is then treated with aqueous sodium hydroxide solution until the pH is between 10 and 11. The organic layer is separated and the aqueous fraction is extracted with dichloromethane (75 ml). The combined organic solution is dried over magnesium sulphate and filtered. The filtrate is added to a solution of diethyl L-tartrate (45.34 g) in dichloromethane (176ml), followed by a solution of titanium isopropoxide (16.36 ml) in dichloromethane (24 ml), and the solution is cooled to between –19° C. and –21°C. under an atmosphere of nitrogen. It is then treated with a solution of cumene hydroperoxide (24.42 ml) in dichloromethane (22 ml) is added during 20 minutes keeping the mixture between –19° C. and –21° C., then the mixture is stirred at this temperature for 7 hours. It is then treated with dilute hydrochloric acid (1N;250 ml) and the mixture is warmed to room temperature with stirring. The aqueous fraction is separated and washed with dichloromethane (125 ml), then treated with tartaric acid (7.5 g) and toluene (156 ml). The pH is adjusted to 10 by treatment with aqueous sodium hydroxide solution and the toluene fraction is removed. The aqueous fraction is extracted with dichloromethane (5×156 ml), adjusting the pH to 10 for each extraction. The combined dichloromethane and toluene solutions are washed with an aqueous solution of sodium disulphite saturated with sodium chloride, then dried over magnesium sulphate, filtered and concentrated under reduced pressure, to give crude (R)-6-(3-pyridyl)-3,4-dihydro-2H-thiopyran 1-oxide (12.48 g) in the form of a yellow oil.

We claim:

1. (R)-6-(3-pyridyl)-3,4-dihydro-2H-thiopyran 1-oxide.
2. A process for the preparation of (1R,2R)-2-(3-pyridyl) tetrahydro-2H-thiopyran 1-oxide or (1R,2S)-2-(3-pyridyl) tetrahydro-2H-thiopyran 1-oxide, or a mixture thereof, which comprises the stereoselective reduction of (R)-6-(3-pyridyl)-3,4-dihydro-2H-thiopyran 1-oxide.
3. A process according to claim 2 wherein the product is recrystallized and substantially pure (1R,2R)-2-(3-pyridyl) tetrahydro-2H-thiopyran 1-oxide is isolated.
4. A process according to claim 2 wherein the reduction is carried out by means of a metal borohydride.
5. A process according to claim 4 wherein the reduction is carried out by means of sodium borohydride.
6. A process according to claim 4 wherein the reduction is carried out in a lower alcohol.
7. A process for the preparation of (R)-6-(3-pyridyl)-3,4-dihydro-2H-thiopyran 1-oxide which comprises the stereoselective oxidation of 6-(3-pyridyl)-3,4-dihydro-2H-thiopyran.
8. A process according to claim 7 wherein the oxidation is carried out in dichloromethane.
9. A process according to claim 7 wherein the oxidation is carried out in an inert atmosphere.
10. A process according to claim 7, wherein the oxidation is carried out by means of a mixture of a dialkyl L-tartrate with titanium isopropoxide and an organic hydroperoxide.
11. A process according to claim 10 wherein the dialkyl L-tartrate is diethyl L-tartrate or diisopropyl L-tartrate.
12. A process according to claim 10 wherein the organic hydroperoxide is tert-butyl hydroperoxide or alpha,alpha-dimethylbenzyl hydroperoxide.
13. A process according to claim 10 wherein for each equivalent of 6-(3-pyridyl)-3,4-dihydro-2H-thiopyran there is employed at least 0.1 equivalents of titanium isopropoxide, and for each equivalent of titanium isopropoxide there is employed at least 2 equivalents of the dialkyl L-tartrate.
14. A process according to claim 13 wherein for each equivalent of 6-(3-pyridyl)-3,4-dihydro-2H-thiopyran there is employed 0.5 to 1.0 equivalents of titanium isopropoxide, and for each equivalent of titanium isopropoxide there is employed 2 to 4 equivalents of the dialkyl L-tartrate.

15. A process according to claim 3 wherein the (R)-6-(3-pyridyl)-3,4-dihydro-2H-thiopyran 1-oxide is produced by the process of any one of claims 7 to 14.

16. 6-(3-pyridyl)-3,4-dihydro-2H-thiopyran.

17. A process for the preparation of 6-(3-pyridyl)-3,4-dihydro-2H-thiopyran which comprises the reaction of an acid with a 3-(5-alkanoylmercaptopentanoyl)pyridine or a salt thereof.

18. A process according to claim 17 wherein the reaction is preceded by the reaction of a base with the 3-(5-alkanoylmercaptopentanoyl)-pyridine or salt thereof.

19. A process according to claim 10 wherein the 6-(3-pyridyl)-3,4-dihydro-2H-thiopyran is produced by the process of claim 17 or 18.

20. A 3-(5-alkanoylmercaptopentanoyl)-pyridine or a salt thereof.

21. A 3-(5-Acetylmercaptopentanoyl)pyridine or a salt thereof.

22. A process for the preparation of a 3-(5-alkanoylmercaptopentanoyl)pyridine or a salt thereof which comprises the reaction of 4-hydroxybutyl 3-pyridyl ketone with thioacetic acid, diethyl azodicarboxylate and triphenyl phosphine in the presence of a tertiary base followed by reaction with thioacetic acid or an alkali metal salt thereof, followed, if desired, by formation of the desired salt by reaction with the appropriate acid.

23. A process for the preparation of a 3-(5-alkanoylmercaptopentanoyl)pyridine or a salt thereof which comprises the reaction of 4-hydroxybutyl 3-pyridyl ketone with an arylsulphonyl halide or an alkylsulphonyl halide, in the presence of a tertiary base, followed by reaction with thioacetic acid or an alkali metal salt thereof, followed, if desired, by formation of the desired salt by reaction with the appropriate acid.

24. A process according to claim 17 wherein the 3-(5-alkanoylmercaptopentanoyl)pyridine is produced by the process of claim 22.

25. A process according to claim 3 wherein the reduction is carried out by means of a metal borohydride.

26. A process according to claim 25 wherein the reduction is carried out by means of sodium borohydride.

27. A process according to claim 25 wherein the reduction is carried out in a lower alcohol.

28. A process according to claim 11 wherein the organic hydroperoxide is tert-butyl hydroperoxide or alpha,alpha-dimethylbenzyl hydroperoxide.

29. A process according to claim 11 wherein for each equivalent of 6-(3-pyridyl)-3,4-dihydro-2H-thiopyran there is employed at least 0.1 equivalents of titanium isopropoxide, and for each equivalent of titanium isopropoxide there is employed at least 2 equivalents of the dialkyl L-tartrate.

30. A process according to claim 28 wherein for each equivalent of 6-(3-pyridyl)-3,4-dihydro-2H-thiopyran there is employed at least 0.1 equivalents of titanium isopropoxide, and for each equivalent of titanium isopropoxide there is employed at least 2 equivalents of the dialkyl L-tartrate.

31. A process according to claim 29 wherein for each equivalent of 6-(3-pyridyl)-3,4-dihydro-2H-thiopyran there is employed 0.5 to 1.0 equivalents of titanium isopropoxide, and for each equivalent of titanium isopropoxide there is employed 2 to 4 equivalents of the dialkyl L-tartrate.

32. A process according to claim 30 wherein for each equivalent of 6-(3-pyridyl)-3,4-dihydro-2H-thiopyran there is employed 0.5 to 1.0 equivalents of titanium isopropoxide, and for each equivalent of titanium isopropoxide there is employed 2 to 4 equivalents of the dialkyl L-tartrate.

33. A process for the preparation of (R)-6-(3-pyridyl)-3,4-dihydro-2H-thiopyran 1-oxide which comprises the stereoselective oxidation of 6-(3-pyridyl)-3,4-dihydro-2H-thiopyran produced by the process of claim 18, wherein the oxidation is carried out by means of a mixture of a dialkyl L-tartrate with titanium isopropoxide and an organic hydroperoxide.

34. A process for the preparation of 6-(3-pyridyl)-3,4-dihydro-2H-thiopyran which comprises the reaction of an acid with a 3-(5-alkanoylmercaptopentanoyl)pyridine or a salt thereof wherein the 3-(5-alkanoylmercaptopentanoyl) pyridine is produced by the process of claim 23.

35. A process according to claim 18 wherein the 3-(5-alkanoylmercaptopentanoyl)pyridine is produced by the process which comprises the reaction of 4-hydroxybutyl 3-pyridyl ketone with thioacetic acid, diethyl azodicarboxylate and triphenyl phosphine in the presence of a tertiary base followed by reaction with thioacetic acid or an alkali metal salt thereof, followed, if desired, by formation of the desired salt by reaction with the appropriate acid.

36. A process according to claim 18 wherein the 3-(5-alkanoylmercaptopentanoyl)pyridine is produced by the process which comprises the reaction of 4-hydroxybutyl 3-pyridyl ketone with an arylsulphonyl halide or an alkylsulphonyl halide, in the presence of a tertiary base, followed by reaction with thioacetic acid or an alkali metal salt thereof, followed, if desired, by formation of the desired salt by reaction with the appropriate acid.

* * * * *